US011490823B2

(12) United States Patent
Richter et al.

(10) Patent No.: US 11,490,823 B2
(45) Date of Patent: Nov. 8, 2022

(54) METHOD OF DETECTING PORTAL AND/OR HEPATIC PRESSURE AND A PORTAL HYPERTENSION MONITORING SYSTEM

(71) Applicant: Microtech Medical Technologies Ltd., Tel Aviv (IL)

(72) Inventors: Yoram Richter, Ramat Hasharon (IL); Eric S. Tammam, Modiin (IL); Shahar Even-Dar Mandel, Tel Aviv (IL)

(73) Assignee: Microtech Medical Technologies Ltd., Tel Aviv (IL)

( * ) Notice: Subject to any disclaimer, the term of this patent is extended or adjusted under 35 U.S.C. 154(b) by 603 days.

(21) Appl. No.: 16/129,912

(22) Filed: Sep. 13, 2018

(65) Prior Publication Data
US 2019/0008400 A1 Jan. 10, 2019

Related U.S. Application Data
(62) Division of application No. 13/600,437, filed on Aug. 31, 2012, now Pat. No. 10,105,067.
(Continued)

(51) Int. Cl.
*A61B 5/0215* (2006.01)
*A61B 5/00* (2006.01)
(52) U.S. Cl.
CPC ........ *A61B 5/02152* (2013.01); *A61B 5/6876* (2013.01); *A61B 5/6862* (2013.01);
(Continued)

(58) Field of Classification Search
CPC ........ A61B 2562/0247; A61B 2562/12; A61B 5/02152; A61B 5/6862; A61B 5/6876; A61B 5/6882
See application file for complete search history.

(56) References Cited

U.S. PATENT DOCUMENTS 5,010,772 A * 4/1991 Bourland ............... A61B 5/113
  73/172
5,353,800 A 10/1994 Pohndorf et al.
(Continued)

FOREIGN PATENT DOCUMENTS

CN 87103492 12/1987
CN 1293348 5/2001
(Continued)

OTHER PUBLICATIONS

International Search Report and Written Opinion from related PCT Application No. PCT/US2012/053298 dated Jan. 15, 2013, 14 pages.
(Continued)

*Primary Examiner* — Michael T Rozanski
(74) *Attorney, Agent, or Firm* — Cadwalader, Wickersham & Taft LLP

(57) ABSTRACT

The devices and methods generally relate to vibratable sensors for measuring ambient fluid pressure, in particular implantable sensors. The devices and methods are suited to implantation within the body to monitor physiological conditions, such as portal and/or hepatic venous blood pressure, and allow frequent, remote interrogation of venous pressure. The sensor devices are relatively small compared to conventional devices for measuring fluid pressure and can be implanted in the portohepatic venous system, whereas conventional devices are too large. The small size of the device is accomplished by using a thick sensor membrane, compared to conventional devices, and by limiting the size of additional elements of the device relative to the size of the sensor membrane. The thicker sensor member also obviates the need for multiple sensor arrays and maintains the accuracy and robustness of the sensor device. A data capture,
(Continued)

processing, and display system provides a pressure measurement reading.

20 Claims, 7 Drawing Sheets

Related U.S. Application Data

(60) Provisional application No. 61/530,040, filed on Sep. 1, 2011.

(52) U.S. Cl.
CPC ..... *A61B 5/6882* (2013.01); *A61B 2562/0247* (2013.01); *A61B 2562/12* (2013.01)

(56) References Cited

U.S. PATENT DOCUMENTS

| | | |
|---|---|---|
| 5,619,997 A | 4/1997 | Kaplan |
| 6,221,024 B1 | 4/2001 | Miesel et al. |
| 6,248,080 B1 | 6/2001 | Miesel et al. |
| 6,331,163 B1 | 12/2001 | Kaplan |
| 7,134,341 B2 | 11/2006 | Girmonsky et al. |
| 7,331,236 B2 | 2/2008 | Smith |
| 7,415,883 B2 | 8/2008 | Kaplan |
| 8,372,139 B2 | 2/2013 | Bailey et al. |
| 2002/0077673 A1 | 6/2002 | Penner et al. |
| 2004/0097805 A1 | 5/2004 | Verard et al. |
| 2004/0211260 A1 | 10/2004 | Girmonsky et al. |
| 2005/0049499 A1 | 3/2005 | Kaplan |
| 2005/0288590 A1 | 12/2005 | Kaplan |
| 2007/0220986 A1 | 9/2007 | Smith et al. |
| 2008/0312553 A1 | 12/2008 | Timmons |
| 2010/0324378 A1 | 12/2010 | Tran et al. |

FOREIGN PATENT DOCUMENTS

| | | |
|---|---|---|
| CN | 1433661 | 7/2003 |
| CN | 1819855 | 8/2006 |
| CN | 101983031 | 3/2011 |
| EP | 0 809 105 | 11/1997 |
| EP | 1 068 836 A2 | 1/2011 |
| JP | 2000-33079 | 2/2000 |
| JP | 2000-504249 | 4/2000 |
| JP | 2001-61790 | 3/2001 |
| JP | 2002-522155 | 7/2002 |
| JP | 2007-503583 | 2/2007 |
| JP | 2007-256287 | 10/2007 |
| RU | 2 413 190 C1 | 2/2011 |
| UA | 42472 | 7/2009 |
| WO | WO 97/27802 | 8/1997 |
| WO | WO 00/09041 | 2/2000 |
| WO | WO 01/05301 | 1/2001 |
| WO | WO 2004/016341 | 2/2004 |
| WO | WO 2004/096007 A2 | 11/2004 |
| WO | WO 2005/022110 | 3/2005 |
| WO | WO 2005/024367 A2 | 3/2005 |
| WO | WO 2006/035275 | 4/2006 |
| WO | WO 2009/132396 A1 | 11/2009 |
| WO | WO 2010/135048 | 11/2010 |

OTHER PUBLICATIONS

Office Actions and Response of related U.S. Appl. No. 13/600,437: Notice of Allowance and Examiner Initiated Interview Summary dated Jun. 13, 2018; Amendment and Response to Non-Final Rejection with Extension of Time dated Nov. 27, 2017; Non-Final Rejection dated Aug. 11, 2017; Amendment and Response to Final Rejection with Request for Continued Examination dated Mar. 9, 2017; Final Rejection dated Dec. 9, 2016; Amendment and Response to non-Final Rejection dated Jul. 25, 2016; Non-Final Rejection dated Apr. 25, 2016; Amendment and Response to Non-Final Rejection dated Dec. 28, 2015; Non-Final Rejection dated Sep. 25, 2015; Amendment and Response to Final Rejection with Request for Continued Examination and Extension of Time dated Apr. 22, 2015; Applicant Initiated Interview Summary dated Mar. 13, 2015; Advisory Action and After Final Consideration Program Decision dated Jan. 29, 2015; Response to Final Rejection and After Final Consideration Program Request dated Jan. 15, 2015; Final Rejection dated Oct. 22, 2014; Amendment and Response to Non-Final Rejection with Extension of Time dated Sep. 29, 2014; Non-Final Rejection dated May 27, 2014; Response to Election/Restriction dated Feb. 6, 2014; and Requirement for Restriction/Election dated Dec. 19, 2013.

Extended European Search Report and Written Opinion for EP Application No. 19209381.3, publication No. EP 3628319 dated Feb. 12, 2020, 7 pages.

\* cited by examiner

METHOD OF DETECTING PORTAL AND/OR HEPATIC PRESSURE AND A PORTAL HYPERTENSION MONITORING SYSTEM

CROSS-REFERENCE TO RELATED APPLICATIONS

This application is a divisional of U.S. patent application Ser. No. 13/600,437, filed Aug. 31, 2012, now U.S. Pat. No. 10,105,067, which claims the benefit of priority to U.S. Provisional Application No. 61/530,040, filed on Sep. 1, 2011, all of which applications are incorporated herein by reference in their entirety.

FIELD OF INVENTION

The method and apparatus generally relate to measuring ambient pressure in systems comprising incompressible fluids. More precisely, the method and apparatus relate to monitoring blood pressure, and the corresponding blood pressure gradient, between the portal and hepatic veins which together comprise the porto-hepatic venous system, via a small, passive, sensor that is deployed (implanted) in the portal vein only or in both the hepatic and portal veins. The sensor is capable of implantation in the porto-hepatic venous system due to its reduced dimensions, as compared to current sensors for measuring fluid pressure which are too large and invasive to allow frequent, accurate monitoring of porto-hepatic blood pressures. The implanted sensor measures portal vein blood pressure and/or the porto-hepatic venous pressure gradient by correlation between the blood pressure and the frequency response of the sensor, and may be used in a system which provides pressure readings via an external processing and display system.

BACKGROUND

The portal vein is a vessel in the abdominal cavity that drains deoxygenated blood to the liver for cleaning. A system of blood vessels called the hepatic veins remove the cleaned blood from the liver to the inferior vena cava, where it is returned to the heart. Portal hypertension ("PHT") occurs when the portal vein experiences a rise in blood pressure that is not a consequence of an increase in a patient's overall systemic blood pressure. Often, PHT is defined according to a "portal pressure gradient," or, the difference in pressure between the portal vein and the hepatic veins, for example of 10 mmHg or greater. A typical portal venous pressure under normal physiological conditions is less than or equal to approximately 10 mmHg, and the hepatic venous pressure gradient (HVPG) is less than approximately 5 mmHg. Increased portal pressure leads to the formation of porto-systemic collaterals; the most serious of them being gastroesophageal varices. Once formed, varices represent a major risk for the patient due to the susceptibility for rupture and subsequent hemorrhage that in many cases leads to death. As a result, PHT is considered the most severe complication of cirrhosis of the liver and is the major cause of morbidity and mortality in cirrhosis patients.

Current procedures for monitoring portal pressure generally involve an indirect measurement of the portal venous pressure through the hepatic venous system. One such procedure is known as the hepatic venous pressure gradient or HVPG. HVPG is used to provide an indirect measurement of the portal vein pressure. The procedure is minimally invasive and involves catheterization of the hepatic venous system via femoral vein or jugular entry. A balloon tipped radiolucent catheter that is capable of measuring local blood pressure usually via a pressure transducer is placed in the Inferior Vena Cava or a large hepatic vein segment. Once in place the pressure is measured to provide the free hepatic venous pressure or FHVP. The FHVP is measured to quantify the external pressures being applied to the venous systems and to zero out the effects of systemic pressure. The catheter is then advanced into a small branch and a complete obstruction of flow is created (wedge position usually done by inflating balloon) to provide the wedged hepatic venous pressure or WHVP. The HVPG is given by HVPG=WHVP−FHVP. While the HVPG has been shown to be a very effective diagnostic and prognostic indicator, it has been limited by the invasiveness of the procedure and the need for standardization to provide reliable results.

Other indirect procedures include, for example, measurement of variceal pressure which employs esophago-gastric approaches to advance an inflatable balloon-catheter into the abdomen of patients via the esophagus and stomach and position the balloon, adjacent to a gastroesophageal varix. The force of inflation required against the wall of the varix is used to calculate the intravariceal blood pressure. In general, non-direct portal venous pressure measurement is less precise, while still invasive and uncomfortable for a patient.

Direct measurement of the portal vein has been attempted in the past. One such procedure involves puncture catheterization, wherein a radiologist accesses the portal and/or hepatic venous systems, under fluoroscopic guidance, by puncturing the tissue of the system with a needle or catheter from outside of the system. Using puncture catheterization, the portal vein may be accessed via a transhepatic puncture using either an intracostal or subxiphoid approach, wherein a needle or catheter is inserted at a patient's $12^{th}$ vertebrae, between the ribs, and punctures through to the portal vein. The hepatic venous system may be accessed via a transjugular approach, wherein a needle or catheter is inserted into the jugular vein and advanced into the hepatic vein via the vena cava. The portal vein may also be accessed from the hepatic venous system, using an intrahepatic puncture from the hepatic to portal venous systems. Thus, in order to monitor a portal pressure gradient, two separate punctures (for the portal and hepatic veins) are required. Physicians are reluctant to perform frequent, direct portal vein pressure measurements, due to the invasiveness of the procedure and as a result, it is not clinically practiced.

There exists a strong clinical need for a pressure monitoring system that can provide accurate pressure measurements of portal and/or hepatic blood pressure while allowing the physician to monitor those pressures non-invasively. Conventional devices include active electronics, sensors, and controls which require a power supply, or a connection to the outside world, and which increase the size of conventional devices thus restricting their use in the porto-hepatic venous system. In addition, conventional devices rely on components, for example sensors and/or membranes, that are large and/or needed in plurality of sensors/membranes, in order to maintain functionality, due, in part, to their tendency to rupture.

A need therefore exists for a pressure measurement system that is small in size, sensitive in function, and does not require redundancy. In addition, a need exists for a sensor system that may be operated without the need for wires or cables to transmit the pressure experienced by the sensor to an external device. The pressure measurement system should be miniature, passive, implantable and wireless to allow for non-invasive, frequent monitoring of portal venous pressure.

SUMMARY OF THE INVENTION

The present invention relates to a method and apparatus for measuring portal and/or hepatic pressures. The apparatus is a sensor device that is miniature, passive, implantable and wireless, to allow for non-invasive, frequent monitoring of portal venous pressure. The sensor device is miniature to allow for safe implantation into the target vessels. In one embodiment, the sensor device structure comprises a single sensor unit having a sensor membrane of a thickness greater than at least 1 micron and an overall sensor device size range of 0.1 mm-1 mm in width (w), 0.1 mm-1 mm in depth (d), and 0.1 mm-0.75 mm in height (h). The overall volume of the sensor device will preferably not exceed 0.3 cubic millimeters. Other examples of volumetric ranges (in $mm^3$) for the sensor device are, e.g., 0.005-0.008, 0.01-0.09, or 0.1-0.3. The apparatus is passive to allow the treating physician to monitor the patient as often as is desired or needed. The invention is useful for interrogating ambient conditions in systems that comprise an incompressible fluid particularly in measuring portal and/or hepatic pressures.

One object of the present invention is to provide a sensor device for measuring ambient fluid pressure in a system comprising an incompressible fluid, e.g., a liquid. The sensor device may be a naked vibratable sensor or a vibratable sensor housed in a cavity with or without a bottom film sealing the housing. In one embodiment, the sensor device comprises a vibratable sensor having a sensor membrane, which sensor membrane has a resonance frequency responsive to ambient fluid pressure conditions. The sensor membrane has a thickness in the range of 1 micron-200 microns and forms one side of a chamber. The chamber is defined by the sensor membrane and a plurality of walls which are substantially perpendicular to the sensor membrane. The chamber may be sealed with a compressible gas of predefined pressure disposed therein. The chamber is sealed with a bonding layer using an anodic bonding process. The bonding layer may provide a means for attachment of the vibratable sensor to an anchoring device. As such, the sensor device comprising a naked vibratable sensor may be a hermetically sealed, substantially or partially non-solid component of any shape having a sensor membrane and a chamber. Alternatively, the vibratable sensor may be an acoustically-active solid, i.e., a sensor membrane without a chamber. In either aspect, the vibratable sensor is biocompatible, i.e., substantially non-reactive within a human body.

In another embodiment, the vibratable sensor may be disposed in a cavity defined by a housing. In this embodiment a cover plate covers the housing cavity such that the bonding layer faces the cover plate. A base plate forms the foundation for the housing. The base plate may contain an orifice exposing the sensor membrane of the vibratable sensor to the bodily environment to be measured. In one aspect of this embodiment, the housing further comprises a bottom film. The bottom film may be semi-permeable or non-permeable to external fluids and/or tissues and may enclose an incompressible fluid.

The present invention also relates to a method for measuring portal and/or hepatic pressure, wherein a sensor device has been implanted in one or both of the portal and hepatic veins, wherein each device has a resonance frequency response that is dependent upon ambient pressure and each device has a predefined, non-overlapping resonance frequency response to pressure comprising the steps of: subjecting each sensor device to ultrasonic vibrations; receiving vibrations elicited in each sensor device by the ultrasonic vibrations, each received vibration including a vibration frequency; determining the resonance frequency response of each device from each elicited vibration frequency; determining the ambient pressure surrounding each sensor device from the frequency response of each sensor device; and in certain circumstances, determining a pressure gradient between each sensor device. Where two sensors are in close proximity to one another, the method further comprises distinguishing the frequency response of each sensor.

In one embodiment, a sensor device may be implanted in the portal vein thereby providing a combination of hemostatic and intra-abdominal pressure. In another embodiment, a sensor device may be implanted in each the hepatic and portal venous systems. Implantation into the portal vein may be carried out via a transhepatic puncture using either an intracostal or subxiphoid approach, while the hepatic vein implantation may be carried out through the transjugular approach. In this way, the system may provide information on the pressure gradient between the hepatic venous systems. In this latter embodiment, the system provides both the porto-hepatic pressure gradient and the portal venous pressure in the same session. Implanting the sensor may also include the steps of anchoring the sensor to a bodily tissue or organ, or securing the sensor to a scaffold and implanting the scaffold.

In another embodiment, a sensor device may be implanted in each of the hepatic and portal venous systems. For example, the portal implantation may be performed by a transjugular approach and then traversing a transjugular intrahepatic portosystemic (TIPS) shunt for access to the portal system. In this embodiment the measured porto-hepatic pressure gradient may provide the physician with a method of non-invasively monitoring the patency of the TIPS shunt.

A further object of the invention is to provide a method for measuring portal vein pressure, with an implanted and anchored sensor device in the portal vein comprising the steps of: applying low- and high-frequency acoustic waves to the sensor, receiving the frequencies elicited in the sensor by the low- and high-frequency waves, and processing the received frequencies as acoustic data in order to determine the frequency response, e.g., resonance frequency, of the vibratable sensor, and thereby determine the ambient fluid pressure of the environment in which the sensor is disposed.

An additional object of the invention is to provide a method for detecting and/or monitoring portal hypertension, wherein an implanted sensor device has a frequency response to ambient pressure conditions and at least one frequency response per given pressure comprising the steps of: transmitting low-frequency acoustic waves from a low-frequency acoustic transmitter, transmitting high-frequency acoustic waves from a high-frequency acoustic transmitter, and receiving reflected high-frequency acoustic waves with a high-frequency acoustic receiver and determining a pressure gradient wherein a raised pressure gradient is indicative of an active portal hypertension condition in need of treatment. Under normal physiological conditions the gradient between the portal and hepatic venous pressures is less than about 10 mm Hg. PHT is often defined as a gradient of 10 mm Hg or more. The method may further comprise capturing, processing, and displaying the received high-frequency acoustic waves as acoustic data.

Another object of the invention is to provide a method for measuring ambient fluid pressure in a subject system, from a sensor device disposed in the subject system, where the sensor device includes a vibration sensor with a sensor membrane that has a resonance frequency response dependent on ambient pressure conditions and at least one frequency response per given pressure, comprising the steps of: subjecting the sensor to low- and high-frequency acoustic waves in order to elicit acoustic resonances, or vibrations, in the sensor, detecting the acoustic resonances as reflected signals from the sensor, and processing the detected acoustic resonances in order to determine ambient fluid pressure.

DETAILED DESCRIPTION OF THE INVENTION

The method and apparatus of the invention generally relate to measuring ambient pressure in a system comprising an incompressible fluid. For purposes of this application, "incompressible fluid" refers generally to non-vapor, non-compressible, flowable media, such as liquids, slurries and gels. In particular, the method and apparatus relate to devices which are implanted in a body to monitor hepatic and/or portal venous pressure. The miniature size of the apparatus, compared to current conventional devices for measuring ambient fluid pressure, and relatively low invasiveness of the apparatus and method are particularly well suited to medical and physiological applications, including, but not limited to, measuring: i) blood vessel/artery/vein pressures such as, for example, in portal hypertension; ii) spinal fluid pressure in brain ventricles; iii) intra-abdominal pressures such as in the urinary tract, bladder, kidney, and bile ducts; and the like. The method may be applicable to any disease or condition involving bodily systems through which fluids, i.e., incompressible fluids, e.g., liquids, flow.

The invention is discussed and explained below with reference to the accompanying drawings. The drawings are provided as an exemplary understanding of the invention and to schematically illustrate particular embodiments and details of the invention. The skilled artisan will readily recognize other similar examples equally within the scope of the invention. The drawings are not intended to limit the scope of the invention as defined in the appended claims.

Figure 1:
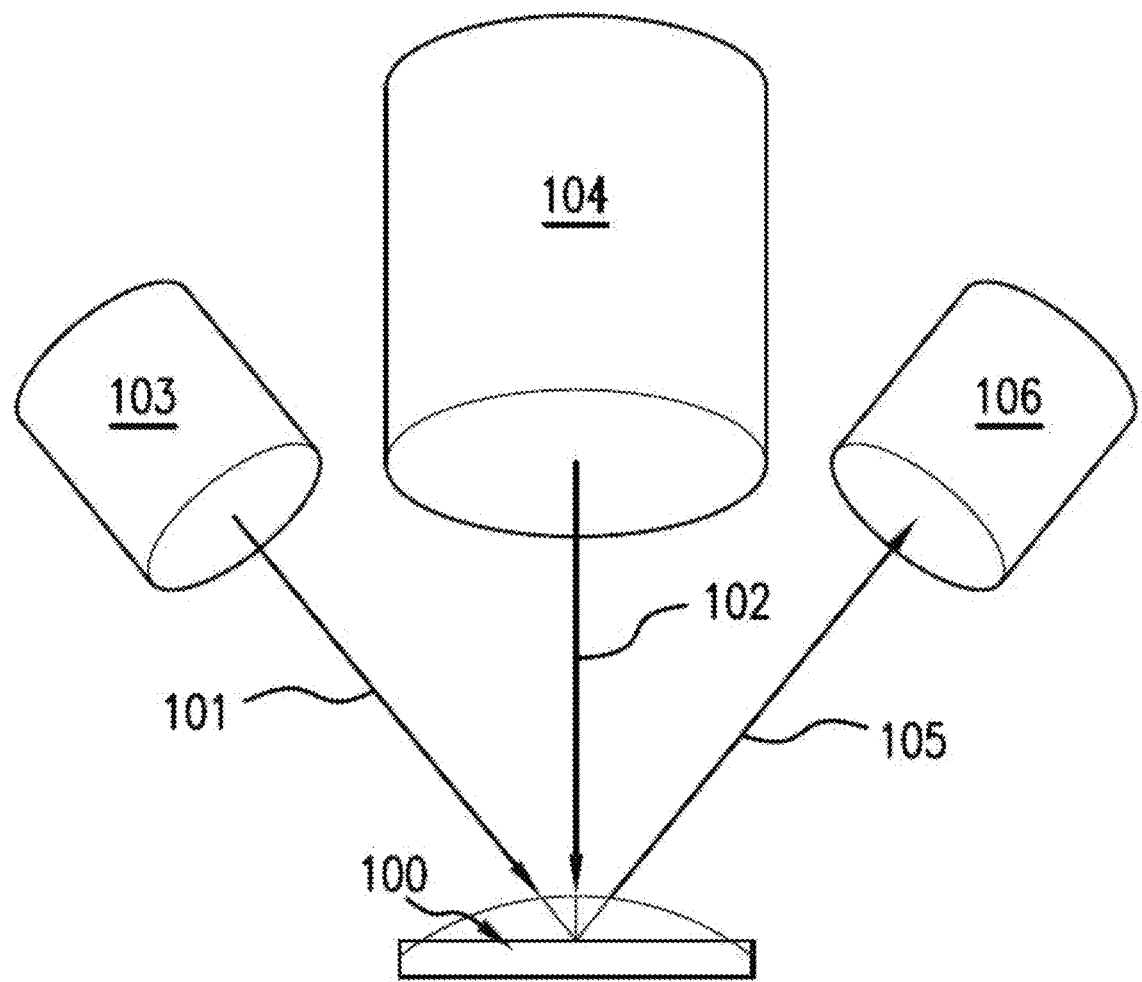
FIG. 1 shows a device in accordance with the invention for measuring portal venous pressure.

FIG. 1 illustrates a sensor device system of the invention. Sensor device 100 measures ambient pressure of the implanted sensor device. Sensor device 100 is subjected to high frequency acoustic waves 101 and low frequency acoustic waves 102 which are generated by high frequency transmitter 103 and low frequency transmitter 104, respectively. High frequency transmitter 103 and low frequency transmitter 104 may comprise any transducer suitable for controllably generating acoustic energy beams (such as, but not limited to sonic or ultrasonic beams) as is known in the art. Typically such transducers are called tactile transducers and are capable of converting an electrical signal into, for example, vibrations that may be felt or used for work. The transducers provide a field of view comprising a depth of penetration of 4-16 cm and a beam spot diameter of 3 cm generating a measurement ellipsoid, for example. The transducers may be implemented using suitable piezoelectric transducers, but other transducers known in the art may be used, such as, but not limited to, capacitive transducers, wideband capacitive transducers, composite piezoelectric transducers, electromagnetic transducers, various transducer array types and various suitable combinations of such transducers configured for obtaining different frequencies and/or beam shapes. For example, acoustic transmitters manufactured by Vemco, PCB Piezoelectronics, and Hardy Instruments may be used. Acoustic waves 101, 102 are directed at the sensor device 100, producing modulated acoustic waves 105 that are detected by high frequency receiver 106. Subsequent processing of waves 105 enables calculation of the ambient pressure in device 100.

One aspect of the invention relates to an implantable sensor device comprising a miniature sensor device for measuring ambient fluid pressure. The sensor device comprises a vibratable sensor having a sensor membrane, which has a frequency response to ambient pressure conditions. The sensor membrane of the vibratable sensor forms one side of a chamber wherein resides a compressible gas of predefined pressure. The chamber is further defined by at least one wall which is preferably substantially perpendicular to the sensor membrane. In one embodiment, the vibratable sensor is made of silicon, but other suitable materials may be used, for example a metal, Pyrex® or other glass, boron nitride, or the like. Non-limiting examples of metals include, e.g., Titanium, Gold, Stainless Steel, Platinum, Tantalum, or any suitable metal, alloy, shape memory alloy such as NITINOL®. The chamber may be sealed with a bonding layer forming a side of the chamber opposite the sensor membrane. Where the vibratable sensor includes a bonding layer for sealing the chamber, the bonding layer may also be used for attachment to an anchoring means. In one embodiment, the bonding layer provides a hermetic seal for the chamber disposed in the vibratable sensor. The bonding layer may comprise Pyrex®, glass, silicon, or other suitable materials.

Generally, the vibratable sensor is manufactured by etching the appropriate shape and materials from a larger panel of the material. For example, the larger panel of material may be covered with a mask, the mask defining the shape of a plurality of the desired vibratable sensors, and then subjected to etching, which may be, for example, chemical etching or physical etching. The mask protects those areas of the panel that must not be removed during the etching process in order to produce the desired shape. For example, a plurality of vibratable sensors is formed when a mask having a plurality of precisely measured cut-outs cover a larger panel of material during the etching process, until chambers of the desired shape are produced in the larger panel to a depth that is substantially equal to a cut-out in the mask. The depth of the chamber may be controlled by various factors, for example where chemical etching is used: the volatility, duration, and number of chemical treatments. Each vibratable sensor may then be cut from the larger panel by slicing between consecutive chambers such that the amount of material remaining on each side of the chamber will be the thickness of walls defining a chamber in the vibratable sensor. The amount of material remaining between the bottom surface of the chamber and bottom of the larger panel will be the thickness of the sensor membrane. Any material that requires joining may be connected, for example, by brazing or welding.

As noted above, the vibratable sensor may additionally include a bonding layer of, for example, Pyrex® or other suitable material, in order to hermetically seal the vibratable sensor, preferably by joining the bonding layer to the walls of the chamber such that the bonding layer and sensor membrane are substantially parallel. In one embodiment, the bonding layer and sensor membrane form opposite walls of a vibratable sensor chamber. The bonding layer may provide a surface for attachment to anchors or other components.

Figure 2:
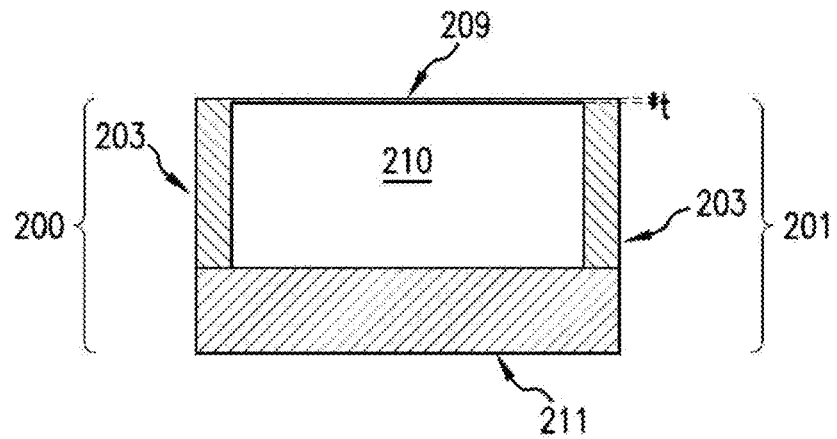
FIGS. 2, 2A and 2B show a sensor in accordance with the invention for measuring portal venous pressure.

FIG. 2 shows a cross sectional illustration of one embodiment of the sensor device 200. In this embodiment, the sensor device 200 is a substantially cubic vibratable sensor 201. As such, the sensor device 200 of FIG. 2 comprises a sensor membrane 209 and chamber 210 which is sealed by bonding layer 211, as described above. The sensor membrane 209 is comparatively thick relative to other remotely operated vibratable fluid pressure sensors. The sensor membrane 209 has a thickness in the range of 1 micron-200 microns. Some exemplary but non-limiting thicknesses include 1.5 microns, 2 microns, 2.5 microns, and 5 microns. The sensor device 200 of the invention retains its accuracy despite the comparatively thick sensor membrane 209. The use of a single sensor (as compared to the plurality of sensors required by prior art remotely-operated vibratable sensors) reduces the overall size of sensor device 200 compared to such conventional devices, making sensor device 200 suitable for use in the porto-hepatic venous system.

The vibratable sensor 201 has a height h, width w, and depth d. In one embodiment, the vibratable sensor 201 measures 0.3 mm (h)×0.5 mm (w)×0.5 mm (d). The width and depth of the vibratable sensor may be equal resulting in a substantially cubic structure. However, the dimensions of the vibratable sensor 201 may generally be any dimensions that do not exceed a maximum volume of about 0.3 mm$^3$, preferably having a size of equal to or less than 0.125 mm$^3$. A minimum volume for the vibratable sensor 201 is about 0.008 mm$^3$. Various alternative embodiments of the vibratable sensor 201 have volumetric ranges (in mm$^3$) of, e.g., 0.005-0.008, 0.01-0.09, or 0.1-0.3, as use requires. Vibratable sensor 201 may be solid, or may be a hermetically sealed, substantially non-solid component, of any shape, which includes sensor membrane 209 and chamber 210, in the example illustrated by FIG. 2. Sensor membrane 209 in the illustrated example is a side of the chamber 210 of the vibratable sensor 201. The depth of the chamber 210 is defined by the height (h) of the walls 203 of the vibratable sensor 201. The sensor membrane 209 may have a thickness (t) on the order of about 2 microns in thickness (t), but more generally, the thickness (t) of the sensor membrane 209 is greater than one micron and less than or equal to 200 microns. Thickness (t) is measured along the height dimension (h) as depicted in FIG. 2.

Vibratable sensor 201 may comprise the cropped rectangular overall shape illustrated in FIG. 2, or one or more other suitable shapes, including but not limited to a sphere, pyramid, trapezoid, or other symmetrical or non-symmetrical shape. In one embodiment, the vibratable sensor 201 comprises silicon. In another embodiment vibratable sensor 201 comprises titanium or another acoustically active material. In other embodiments, vibratable sensor 201 comprises a rubber, polymer, and/or a ceramic material. Alternatively, the vibratable sensor 201 may comprise any suitable material capable of being excited by acoustic stimulation. As used in this application, "silicon" refers to silica and silicates, glasses, cements, and ceramics; it also refers to the class of silicones for which it is a constituent element, including various synthetic plastic and rubber substances made of silicon, oxygen, carbon and hydrogen, for example.

Figure 2A:
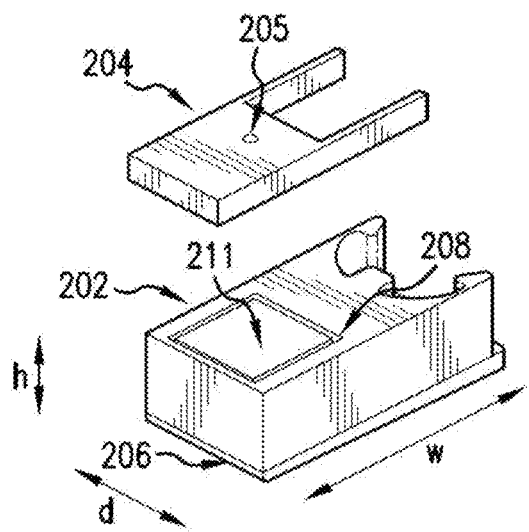
Figure 2B:
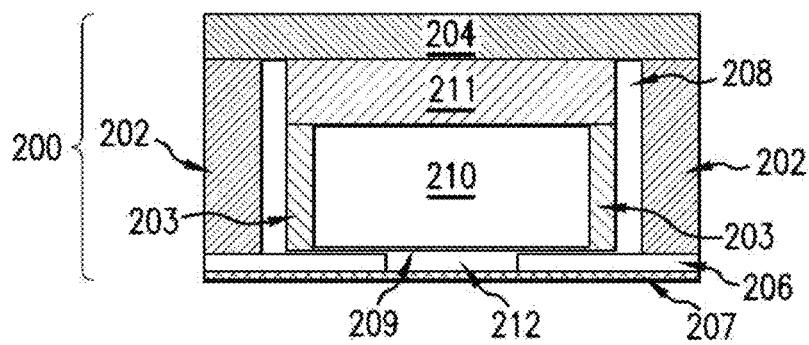

In other embodiments of the sensor device 200, illustrated in FIGS. 2A and 2B, the vibratable sensor is disposed in a cavity 208 defined by a housing 202. The housing 202 encloses the sides of the vibratable sensor 201 but not all or part of the sensor membrane (209 in FIGS. 2 and 2B, unnumbered in FIG. 2A), and the bonding layer 211 faces a cover plate 204 which is mechanically fixed to one side of the housing and serves as a surface for attachment to an anchoring means in certain embodiments. In one aspect of the embodiment illustrated in FIG. 2A, the cover plate 204 may include a fill port 205. The fill port 205 may be used to fill the cavity 208 with an incompressible fluid. As illustrated in FIGS. 2A and 2B, the housing 202 is disposed atop a base plate 206, which provides a foundation for the housing 202 and holds the vibratable sensor 201 inside the cavity 208. The base plate 206 may contain an orifice 212, as shown in FIG. 2B, which exposes the sensor membrane 209 to acoustic activity thereby allowing vibrations to reach and return from vibratable sensor 201.

In the particular embodiment illustrated in cross-sectional view in FIG. 2B the vibratable sensor 201 is disposed in cavity 208 of housing 202, wherein the orifice 212 in base plate 206 exposes all or a portion of the sensor membrane 209 of vibratable sensor 201 to an acoustically transparent bottom film 207. Bottom film 207 is designed to allow for the transmission of acoustic waves, hydrostatic and hydrodynamic pressures from the surrounding environment. Depending upon the choice of material used for the bottom film 207, it may also function to protect the sensor. When the bottom film 207 comprises a semi permeable material, the film protects the vibratable sensor from direct exposure to bodily tissues or other solid bodily matter. When the bottom film 207 comprises an impermeable material, the film 207 may completely protect the vibratable sensor from all bodily fluids and/or materials. In an embodiment wherein the bottom film 207 is impermeable to all fluids and solids, a fill port (not shown in FIG. 2B) may be used to fill the cavity 208 with an incompressible fluid. Bottom film 207 comprises any suitable bioinert material or combinations thereof, including but not limited to, titanium, gold, stainless steel, platinum, tantalum, or any suitable metal, alloy, shape memory alloy such as NITINOL®, silicon, glass, quartz, a ceramic material, a composite material, a metallic or non-metallic nitride, boron nitride, a carbide, a metal oxide, a non-metallic oxide, a polymer based material, a gel, and combinations thereof. Alternatively, bottom film 207 may comprise titanium in one embodiment, for example diffusion-bonded Grade I titanium. In various embodiments, bottom film 207 may substantially seal vibratable sensor 201 in cavity 208, for example when bottom film 207 comprises a substantially non-porous material, or bottom film 207 may be porous, to varying degrees, and expose vibratable sensor 201 to bodily fluids and/or tissues. In the embodiment shown in FIG. 2A, described above, bottom film 207 is absent from base plate 206. In such an embodiment, the vibratable sensor 201 would be completely exposed to the ambient environment via orifice 212.

Cover plate 204, housing 202, and base plate 206 may each comprise any suitable bioinert materials or combinations thereof, including but not limited to titanium, gold, stainless steel, platinum, tantalum, or any suitable metal, alloy, shape memory alloy such as NITINOL®, silicon, glass, quartz, a ceramic material, a composite material, a metallic or non-metallic nitride, boron nitride, a carbide, a metal oxide, a non-metallic oxide, a polymer based material, a gel, and combinations thereof. Alternatively, base plate 206 may comprise a Pyrex® material. Base plate 206, housing 202, and cover plate 204 comprise titanium in one embodiment, for example Grade I titanium. These components may be formed and assembled from separate pieces or may be formed as one element or combined elements to function as described above.

In the embodiment depicted by FIG. 2B, the vibratable sensor 201 contained in the housing cavity 208 may be surrounded by bodily fluid, e.g., blood-flow, which enters the cavity 208 via a porous or absent bottom film 207. Alternatively, the vibratable sensor 201 may be surrounded by an incompressible fluid that is sealed in cavity 208 by a substantially solid or impermeable bottom film 207, after the incompressible fluid is introduced to cavity 208 through fill port 205. A substantially solid bottom film 207 also prevents the introduction of bodily fluids and/or tissues into cavity 208.

Base plate 206 is relatively thin (in the h direction), generally, compared to the overall height of the device as shown in FIGS. 2A, 2B. In one embodiment, base plate 206 represents, for example, 100 microns of an approximately 500 micron overall device height. In other embodiments, base plate 206 may be 5%-20% of the overall device height, but is generally less than or equal to 40% of the overall device height. The height of the base plate 206 should generally be minimized to allow for a maximum cavity 208 volume, which contributes to the accuracy of the device and therefore an overall reduced size when compared to conventional, vibratable sensors having a housing. The base plate 206 also provides a foundation for the device assembly, and absorbs mechanical stresses by providing a sink material (a material to absorb force or energy) where such stresses may dissipate.

Bottom film 207 may be bonded to all or a portion of the base plate 206 and provides further tolerance for stresses. The relatively thin bottom film is generally on the order of 1-10 microns. In one embodiment, the bottom film 207 is desirably 4 microns in thickness. The thin bottom film 207 is generally more pliable than thicker components of the device and may absorb stresses from, for example, expansion and contraction due to changing temperatures. Bottom film 207 is designed to allow for the transmission of acoustic waves, hydrostatic and hydrodynamic pressures from the surrounding environment.

As illustrated in FIG. 2B, cover plate 204 is substantially parallel to base plate 206, and base plate 206 is substantially parallel to, and disposed on, bottom film 207. FIG. 2B shows a cross-section of the sensor having a wafer-style stacking of the bottom film 207, base plate 206, vibratable sensor 201, housing 202, and cover plate 204, wherein the layers may be hermetically sealed and the vibratable sensor 201 is disposed in the cavity 208 of the housing 202 in the illustrated embodiment. Techniques for hermetically sealing the layers of the sensor include but are not limited to diffusion bonding. In certain embodiments, bottom film 207 is sealed by controlled environment methods that minimize oxygenation and other impurities of the bottom film, where conventional, uncontrolled sealing techniques may damage the bottom layer 207. Remaining volume within the cavity 208 may be filled with an incompressible fluid, through the fill port 205 (FIG. 2A) of the cover plate 204. After filling is complete, fill port 205 is temporarily or permanently sealed with different welding technologies such as, for example, arc, laser, resistance, ultrasonic, or torsional, or by diffusion bonding, swedging, adhesives gaskets, capillary seals, or other suitable means for sealing. The manufacturing and assembly method is detailed herein below with respect to the description of FIG. 4.

The overall size of the sensor device 200 depicted in FIG. 2, which is desirably extremely small compared to conventional wireless devices for measuring fluid pressure, may be 0.1 mm-1 mm in width (w), 0.1 mm-1 mm in depth (d), and 0.1 mm-0.75 mm in height (h). In one embodiment, the sensor device 200 has an equal width and depth, forming a substantially cubic structure. Generally, the overall volume of the sensor device will not exceed 0.3 cubic millimeters. For the embodiment shown in FIGS. 2A, 2B, housing 202 has a minimum wall thickness of 300 microns. Base plate 206 has a height, h of approximately 100 microns. Further, base plate 206 is relatively thin compared to the overall height of the sensor device 200 depicted in FIGS. 2A, 2B, which may be, for example, 100 microns (base plate 206) compared to 500 microns (for the overall sensor device). Such a configuration provides more robustness for sensor device 200. In addition, cavity 208 desirably has a height of approximately 400 microns—measured from the surface of base plate 206 abutting cavity 208 to the surface of cover plate 204 abutting cavity 208—but is at least 100 microns in height, and is relatively large compared to the overall height of the device, 400 microns (cavity) versus 500 microns (height of the overall sensor device) in the example of FIGS. 2A, 2B.

The above principles allow for an overall reduction in size from conventional wireless devices for measuring fluid pressure, because the above principles allow for a relatively thick (greater than 1 micron, for example, 2 microns) sensor membrane 209 which is accurate and robust enough to obviate further active components and/or sensor arrays.

Another aspect of the invention relates to a method for determining pressure in the porto-hepatic venous system. Once the sensor device 100 (FIG. 1) is located, data is collected using the transmitter/receiver array 103, 104, 106 as illustrated in FIG. 1. High frequency 101 and low frequency 102 acoustic beams are generated by high frequency 103 and low frequency 104 transmitters, and applied to sensor device 100. Acoustic beams 101, 102 are typically initiated by positioning the transmitters 103, 104 in close but external proximity to the sensor device 100, where "close proximity" is any distance sufficient to apply acoustic beams 101, 102 to sensor device 100 in accordance with the devices and methods herein. Vibrations from the sensor, interrogated and excited by the high frequency 101 and low frequency 102 acoustic beams, create modulated acoustic waves 105, due to the vibration of the vibratable sensor 201 (FIG. 2). Modulated acoustic waves 105 are detected by high frequency receiver 106 which is also placed in close proximity to sensor device 100.

Figure 3:
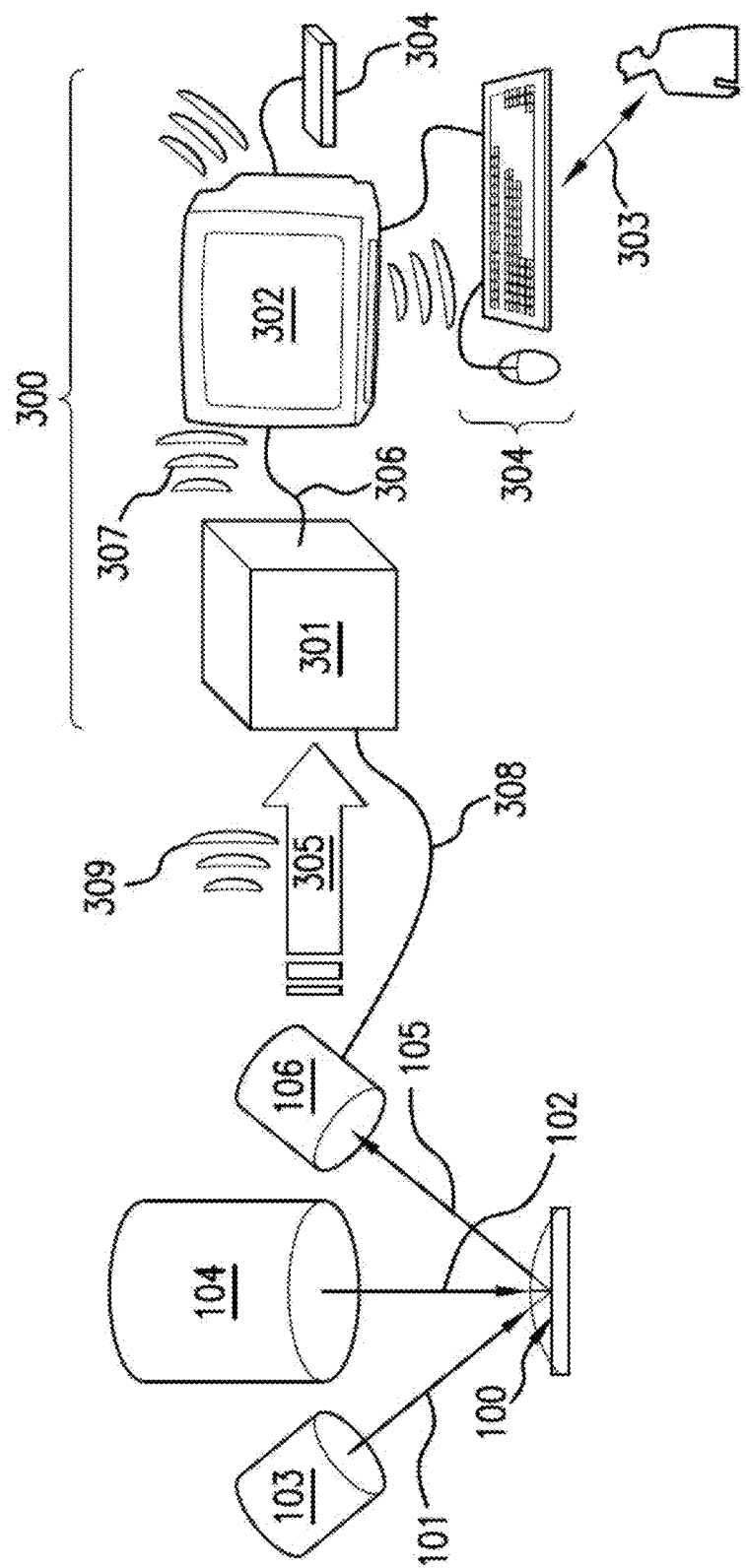
FIG. 3 shows a system in accordance with the invention for measuring, interpreting, and displaying portal venous pressure.

FIG. 3 shows one embodiment of a processing and display system 300 of the system of the current invention and illustrates operation of the sensor device in the system. FIG. 3 makes reference to FIG. 1, which illustrates a generic sensor device 100 of the system of the invention, however the processing and display system 300 of FIG. 3 applies equally to the sensor device 200 as illustrated in FIGS. 2, 2A and 2B. Thus, for purposes of describing the operation of the sensor device and system with reference to FIG. 3, sensor device reference numbers 100 and 200 are used interchangeably.

Referring to FIG. 3, high frequency receiver 106 transmits data 305 to processing unit 301. Data 305 may include radio waves, electrical signals, digital signals, waveform signals, or any other means sufficient for communicating the acoustic properties of modulated acoustic waves 105, as received by high frequency receiver 106. Processing unit 301 interprets data 305 using the properties of modulated acoustic waves 105 to determine a frequency response of the sensor device 100. The frequency response of the sensor is defined herein as the frequency of vibrations, including at least one resonance frequency, emitted by the sensor in response to the transmission of ultrasonic vibrations from transmitters 103, 104, at a given ambient pressure. For example, the frequency response of sensor device 100 is known when sensor device 100 is subject to "normal", i.e., non-symptomatic, physiological conditions. In the portal venous system, "normal" conditions are a pressure approximately 5 mmHg or less, and a pressure gradient between the portal and the hepatic vein of approximately 10 mmHg or less. The internal pressure of sensor device 100—i.e., the pressure within cavity 208—is known and substantially constant. In the portal venous system, the frequency response of sensor device 100 changes in accordance with changes in the venous pressure. Low-frequency acoustic waves 102, for example at 50 kHz, will stimulate at least one frequency response of vibrations in sensor device 100, at a given pressure, by exciting vibrations in vibratable sensor 201 (FIG. 2). High frequency acoustic waves, for example 750 kHz, may be used to interrogate the excited vibratable sensor 201 (FIG. 2). This results in modulated acoustic waves 105 that can be detected by receiver 106. High frequency acoustic waves are meant to interrogate, not to excite, the membrane 209 of the vibratable sensor 201, and preferably minimally interact with the membrane 209 to maximize linearity of the system.

One type of frequency response which may be measured according to the present invention is a resonance frequency. For example, resonance frequency(-ies) of the sensor device 100 may be identified as the frequency(-ies) which exhibit peak vibration amplitudes returned from the sensor device 100. In an alternative embodiment, the resonance frequencies are absorbed by bottom film 207, and therefore do not materialize as vibrations generated by the sensor device 100, and are identified as the frequencies where vibrations are not returned from the sensor device 100, or where the minima of amplitude vibrations returned from sensor device 100 exist. The difference between the actual resonance frequency excited in the sensor device 100 and the resonance frequency of the sensor device under normal conditions is correlated to the difference in pressure between normal conditions and the actual blood pressure. Thus, actual portal venous pressure is calculated based on the measured resonance frequencies of sensor device 100.

In one embodiment of the invention, the low frequency transmitter is an annular low frequency piezoelectric transducer having a working range of 0-100 kHz, 30-100 kHz, or 50-100 kHz, for example, depending on the precision required. It is, however, noted that any other suitable low frequency transducer known in the art may be used for implementing the invention.

In another embodiment of the invention, the high frequency transmitter 103 is an annular high frequency transmitting transducer, implemented as a low noise (i.e., low-range or low-bandwidth) frequency generator unit designed to generate a high frequency acoustic wave 101 at, for example, 750 kHz. It is noted, however, that other different values of the high frequency acoustic wave may also be used in implementing the present invention.

In one embodiment of the invention high frequency receiver 106 is a disc-like high frequency receiving piezoelectric transducer. The annular high frequency transmitter 103 and the high frequency receiver 106 are, for example, a model CLI 7900 general-purpose ultrasonic probe, commercially available from, for example, Capistrano Labs, Inc., San Clemente, Calif., USA. When the acoustic waves including the high frequency acoustic waves 101 and low frequency acoustic waves 102 are directed at the sensor device 100, the high frequency receiver 106 receives the modulated acoustic waves 105 which are excited in the sensor device 100 as well as other noise, e.g., signals that are reflected from other materials in the measurement environment or interference. The high frequency receiver 106 generates an electrical signal representative of the returning acoustic signals that it receives. The electrical signal produced by the receiver 106 is processed by the system described herein, for example as shown in FIG. 3.

In another embodiment, low frequency transmitter 104 has a working range of 30-90 kHz, and transmits acoustic frequencies, for example, at 50 kHz; high frequency transmitter 103 transmits, for example, at approximately 750 kHz with a narrow bandwidth (range); high frequency receiver 106, under the example, operates in the range of 750 (high)±50 (low) kHz. Low frequency transmitter 104, high frequency transmitter 103, and high frequency receiver 106 may alternatively operate in any range suitable for use with the devices and methods disclosed herein, and as particularly required for measuring fluid pressure in particular environments.

High frequency receiver 106 is also a transducer, and is used for receiving the signals returning from the sensor when the sensor is interrogated by the high frequency acoustic waves 101. For example, the transducer may be implemented using suitable piezoelectric transducers, but any other type of transducers known in the art may be used to implement the transducers, such as, but not limited to, capacitive transducers, wideband capacitive transducers, composite piezoelectric transducers, electromagnetic transducers, various transducer array types, cMUTs, cymbal transducers and various suitable combinations of such transducers configured for obtaining different frequencies and/or beam shapes. For example, acoustic receivers manufactured by Vemco, PCB Piezoelectronics, and Hardy Instruments may be used.

Modulated acoustic waves 105 are the result of combining high frequency acoustic waves 101 and low frequency acoustic waves 102 in a reversible manner, in order to achieve a waveform with a desired frequency, wavelength, and/or amplitude. Unmodulated noise, for example caused by reflections of acoustic waves off of materials in the sensor device 100 environment, is thus distinguished from the modulated acoustic waves 105 that are excited by the sensor device 100. When the received signal amplitude (in dB) is analyzed according to the frequency (in MHz), the amplitude peaks at the resonance frequency of the sensor device 100. High frequency receiver 106 communicates the modulated acoustic waves 105 to a processing and display system, detailed in FIG. 3, for interpretation and use.

In one embodiment, vibrations excited in sensor device 100 are distinguished from noise by correlating pressure measurements to a heart rate or pulse measurement. In this embodiment, a plurality of pressure measurements are taken during the interrogation period, for example, at least one cycle of expansion and contraction of the heart (pulse cycle). During the pulse cycle, the pressure of the entire vascular system will change continuously as the heart draws blood in and forces blood out. Accordingly, an acoustic signal that changes in a consistent manner correlated to the pulse cycle demonstrates an excitation in the sensor. Noise reflected from, for example, surrounding tissues in the interrogation environment, does not produce such a continuously changing signal that is correlated to the pulse cycle. The above features are not limited to a single embodiment; rather, those features and functions may be applied in place of or in conjunction with the other embodiments and concepts herein. The pulse cycle and waveform may be measured by an external device, for example using a pulse oximeter, heart rate monitor, ECG, etc. Optionally, such instruments may be connected to the pressure monitoring system of the invention to input the pulse or pulse waveform into the system for correlation with the acquired pressure waveform from the sensor to determine the validity of the acquired signal.

Figure 5A:
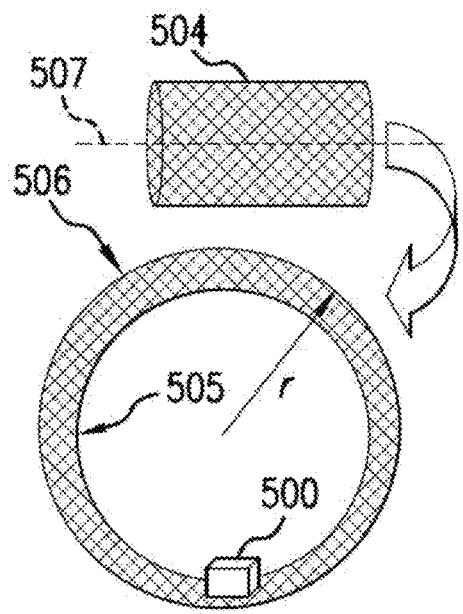
FIGS. 5A-5C show various embodiments of a passive sensor anchoring device in accordance with the invention.

In operation, sensor device 100 is disposed in a measurement environment, for example, implanted in an area, vessel, artery, or the like, where pressure measurements are desired. The sensor system may be implanted by methods including, for example, portal venous catheterization procedures to position the sensor device 500 in the portal vein shown, for example, via scaffoldings 504 illustrated in FIGS. 5A-5C and-FIGS. 6A-6B. In such a procedure a percutaneous transhepatic approach to the portal vein may be employed, for example inserting the cannula 601 into a subject between the ribs and puncturing through to the portal vein. For the hepatic vein, the sensor device 500 may be inserted, for example, by transjugular hepatic vein access, similar to the procedure used in hepatic vein pressure-gradient measurements. In this procedure, a catheter is inserted into the jugular vein in the neck and advanced into the hepatic vein via the vena cava. The portal vein is also accessible by puncture from the hepatic vein, after a catheter has been inserted via transjugular hepatic procedures similar to the implantation of transjugular intrahepatic portosystemic shunts. Implantation into the portal vein may also involve traversing a TIPS shunt, in which case the patency of the TIPS shunt may be non-invasively monitored. Implantation is typically performed by an interventional radiologist under fluoroscopic guidance. Sensor device 500 is guided to the intended position using catheter delivery system 600, for example, as shown in FIGS. 6A-6B. Once deployed in the intended location, sensor device 500 remains in the vessel or area. Other methods for deploying the sensor as are known in the art may alternatively be employed. Non-limiting examples of such deployment methods include, but are not limited to, those described in U.S. Pat. No. 6,331,163 to Kaplan and U.S. Patent Publication No. 2005-0124896 to Richter, which are incorporated herein by reference.

According to one aspect of the invention, the implanted sensor device 100 is subjected to both high and low frequency acoustic waves 101, 102, the latter excites vibrations in the sensor device 100, and the reflected high frequency acoustic waves are then manifested as modulated acoustic waves 105. High frequency receiver 106 receives the modulated acoustic waves 105 and communicates the properties of the modulated acoustic waves 105 to a processing and display system, detailed in FIG. 3, for interpretation and use.

Returning to FIG. 3 which shows one embodiment of a processing and display system 300 of the current invention, data 305 from high frequency receiver 106 is transmitted to a processing unit 301 which determines the pressure of the environment surrounding the sensor device 100. Data 305 is communicated between high frequency receiver 106 and processing unit 301 via a wired 308 or wireless 309 connection. Wired connection 308 is, for example, an electronic cable or integral connection, or the like. Wireless connection 309, for example, operates by transmitting radio waves, acoustic waves, or other known media for remotely communicating data.

Processing unit 301 may comprise a computer, workstation, or other electrical or mechanical device programmed to perform the data conversions and/or displays described herein and as needed for the method of use. By way of a non-limiting example, the invention may be practiced on a standard workstation personal computer, for example those manufactured by Dell, IBM, Hewlett-Packard, or the like, and which typically include at least one processor, for example those manufactured by Intel, AMD, Texas Instruments, or the like. Processing unit 301 also comprises dedicated hardware and/or software, e.g., a data capture system such as the National Instruments PCI-6115 data capture board or may be comprised of a custom designed device for that purpose.

The output of processing unit 301 is a pressure measurement that is converted to a usable, displayable measurement either by processing unit 301 or display unit 302, or a combination thereof. For example, pressure measurements may be reported in numerical units of mmHg or Torr or maybe displayed with relation to a predefined arbitrary scale. Display unit 302 may comprise a monitor, numerical display, LCD, or other audio or visual device capable of displaying a numerical measurement. As shown in the embodiment of FIG. 3, display unit 302 is connected to or integral with processing unit 301 by connection 306, for example in the case of a computer with processing and display units, which optionally includes as a remote element, separate wired element, or integral element to processing 301 and/or display 302 units, interface 303 and input/output elements 304, such as a keyboard, mouse, disk drive, optical pen, or the like, to allow a user to collect, manipulate, track, and record data. Connection 306 may optionally be a remote connection 307, operating by transmission of radio waves, acoustic waves, or other known remote transmission methods.

One aspect of the invention is directed to a method of monitoring PHT. The sensor device 100 may be implanted in either or both of the portal and/or hepatic veins according to the procedures described herein or known. Once implanted in the porto-hepatic venous system, the method comprises the steps of: subjecting the sensor device 100 to ultrasonic vibrations from high frequency 103 and low frequency 104 transmitters; receiving the frequency response of one (or each) of the sensor devices 100; determining a resonance frequency of the (or each) sensor device 100 from the received frequency response; determining ambient fluid pressure surrounding the (or each) sensor device 100 from the resonance frequency of the (or each) sensor device 100; determining a pressure gradient between each sensor device 100 (in each of the portal and hepatic veins) wherein an elevated gradient (generally greater than 10 mm Hg) is indicative of an active portal hypertension condition in need of treatment; and displaying and/or recording the pressure measurements according to the system described with respect to FIG. 3. Thus, the pressure of the portal and/or hepatic veins may be independently interrogated, determined, and displayed. Where the pressure gradient between the portal and hepatic veins is desired, one sensor may be implanted in each of those systems, and data captured for each sensor in the manner described above. The numerical measurement of the hepatic vein pressure, for example, could then be subtracted by further processing from the numerical measurement of the portal vein pressure, providing the gradient, or difference in pressure, between the two systems.

The method of monitoring a pressure gradient between the portal and hepatic veins includes the additional step of delineating between each sensor while performing the interrogation. The mechanism for the differentiation can be one of the following or both: (i) differences in frequency responses between the sensors may be detected by changing the dimensions of the membrane while maintaining the pressure ranges and accuracy of the sensor (i.e., one sensor will have a frequency response at a defined pressure between 30-50 kHz while the other may have a frequency response of 60-80 kHz at the defined pressure). Such a design entails a low frequency transmitter with a wide enough bandwidth to enable the operation of both sensors (i.e., between 30-50 and 60-80 kHz), or two or more low-frequency transmitters, one for each type of sensor; (ii) a narrow high or low (or both) frequency acoustic field is applied to the vicinity of the sensors to precisely locate each sensor during interrogation while acoustically isolating any other sensors in the vicinity.

Figure 7:
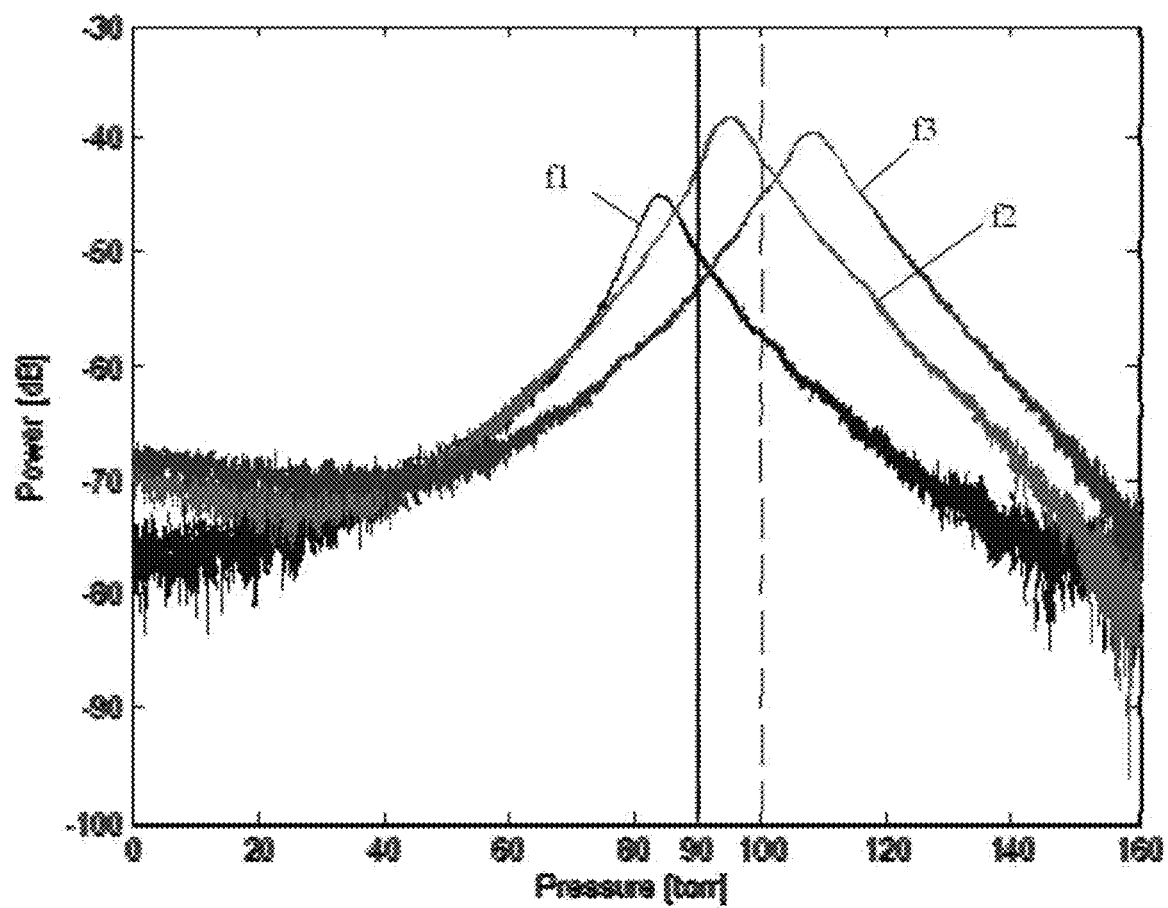
FIG. 7 illustrates exemplary resonance frequencies from a vibration sensor as a function of ambient pressure in response to three different excitation frequencies, based on pressure oscillations around the mean value to be measured.

In one embodiment, determining the pressure in the portal and/or hepatic veins comprises obtaining the mean pressure by a phase inversion method of calculation, which relies on small pressure oscillations created by the heartbeat. The small pressure oscillations exist around the mean pressure value which is to be measured. In order to determine the mean pressure value to be measured, a receiver as described for example with respect to FIG. 3 measures the response power of the sensor device, which is the amplitude of the oscillation of the vibratable sensor and is measured in decibels (dB). As illustrated in FIG. 7, the small pressure oscillations occur around a particular mean value—for example 90 Torr, indicated by the solid vertical line. When the sensor device is excited by certain frequencies, for example f1 and f2, the response power is an increasing function of the pressure, whereas excitation by another frequency, f3, results in a response power that is a decreasing function of the pressure. As a direct result the response power of f1 and f2 oscillate in phase with each other (and with the pressure) and that of f3 oscillates with an opposite phase. When the small pressure oscillations occur around a different mean value—for example 100 torr, indicated in FIG. 7 by the dashed vertical line—the response power of f1 is an increasing function of the pressure, whereas that of f2 and f3 are decreasing functions of the pressure. As a result, the response power of f1 oscillates in phase with the pressure, and that of f2 and f3 oscillated with an opposite phase. The phase inversion algorithm is based on these observations. The resonance frequency of the sensor device at the mean ambient pressure is that around which the phase inversion occurs. In this embodiment, the pulse cycle and waveform may be measured with an external device for correlation with the acquired pressure waveform from the sensor.

This technique is particularly applicable to PHT since only a mean pressure reading is necessary.

Figure 4:
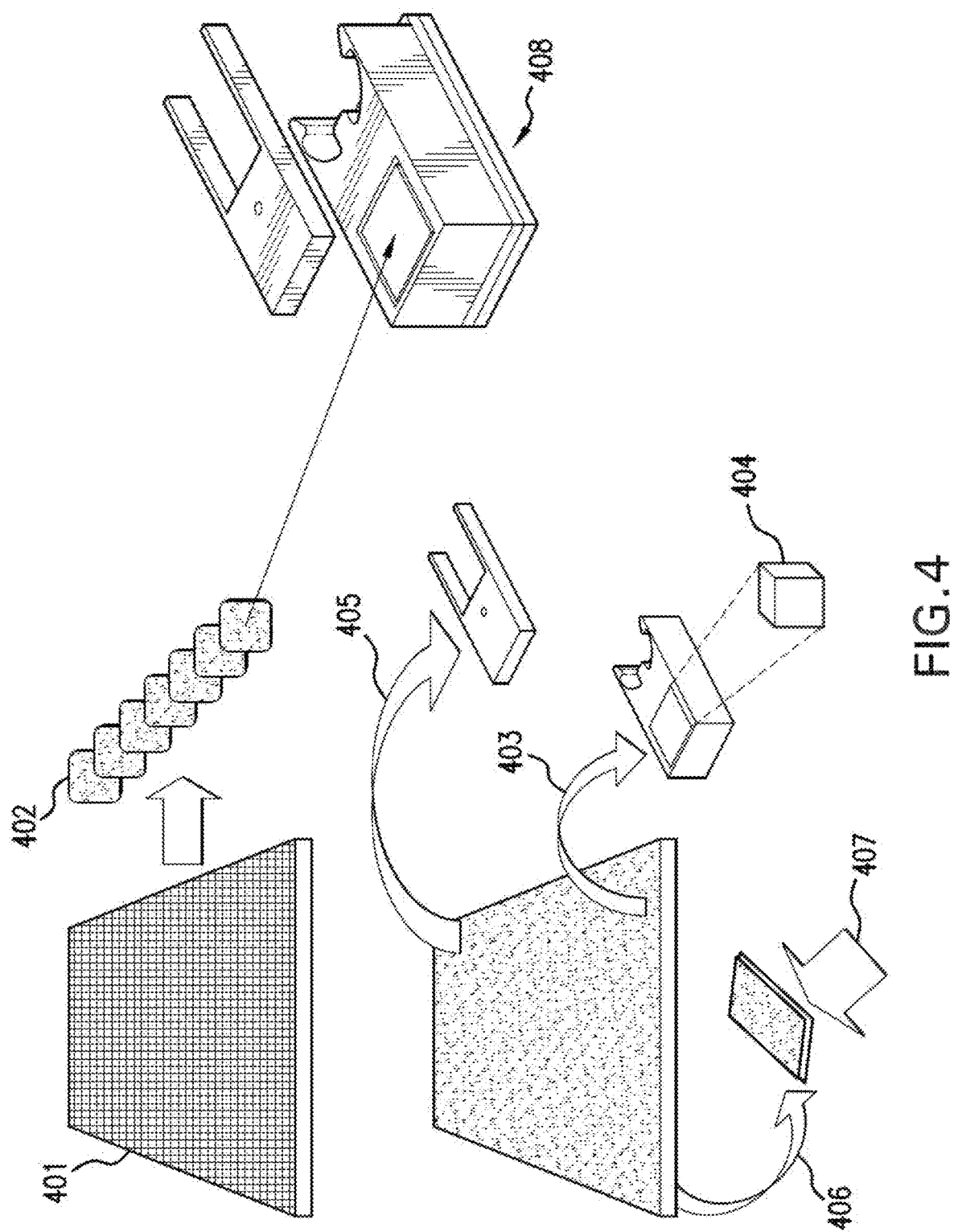
FIG. 4 shows a passive sensor manufacturing method in accordance with the invention.

With reference now to FIG. 4, one example of a manufacturing method embodiment is shown for a sensor device in accordance with the devices and methods described herein. In step 401, vibratable sensors are etched and cut from a panel of material to produce a plurality of individual vibratable sensors 402, each of which may be hermetically sealed with a layer, such as bonding layer 211 (illustrated in FIGS. 2, 2B) made of, for example, Pyrex®, which may be anodically bonded to one side of vibratable sensor 402, or attached by brazing, welding (such as, for example, arc, laser, resistance, ultrasonic, or torsional), diffusion bonding, vapor deposition, adhesives, epoxies, or the like. Each vibratable sensor may then be assembled into a sensor device directly or may be further processed to be inserted into a housing cavity, as described below. Housing defining a cavity may be created in parallel steps, in which an individual housing is etched and cut 403 from larger panels of material and assembled 404 into a housing having a cavity. Cutting is accomplished by any suitable method, e.g., chemical etching, laser cutting, mechanical cutting, plasma cutting, punching, or the like. In a similar fashion if a cover plate is desired, a cover plate and fill port are machined 405 from a larger panel of material. Similarly, a base plate may be machined 406 from a larger panel of material. In one embodiment, a bottom film is hermetically sealed to the face of the base plate opposite the face that will abut the stacked assembly, in step 407, via brazing, welding (such as, for example, arc, laser, resistance, ultrasonic, or torsional), diffusion bonding, vapor deposition, adhesives, epoxies, or the like. In another embodiment, the bottom film is not used. A vibratable sensor is then inserted into the cavity in the housing and the sensor-housing assembly is disposed on a base plate in a wafer-style stacking arrangement 408 (see also FIG. 2B). As part of step 408, the cover plate is disposed on the housing and encloses the vibratable sensor in the cavity, and the base plate and housing, and housing and cover plate, are hermetically sealed via brazing, welding (such as, for example, arc, laser, resistance, ultrasonic, or torsional), diffusion bonding, vapor deposition, adhesives, epoxies, or the like. In a further, non-illustrated step, the empty space of the cavity surrounding the vibratable sensor is filled with an incompressible fluid via the fill port in the cover plate, and the fill port is subsequently hermetically sealed using brazing, welding (such as, for example, arc, laser, resistance, ultrasonic, or torsional), diffusion bonding, or the like.

In the embodiment where the sensor without a housing is desired, the sensor is further manufactured by attaching the vibratable sensor to an anchoring means. In one embodiment, a bonding layer (illustrated as 211 in FIGS. 2, 2B) is attached to the vibratable sensor by brazing, welding, diffusion bonding, vapor deposition, adhesives, epoxies, or the like. The bonding layer provides a surface to attach the sensor to a support structure, for example an anchoring means. The bonding layer and support structure may be joined by brazing, welding, diffusion bonding, vapor deposition, adhesives, epoxies, or the like. In one embodiment, the bonding layer comprises Pyrex®.

The sensor device with or without a housing may be fixed to a desired support structure by various means known in the art. A support structure such as, for example, an annular shaped structure may be pressed against the vessel wall wherein the sensor device is attached thereto. In another embodiment, hooks, tethers, or other fixation devices may be used to fix the sensor into the desired position. FIG. 5A shows attachment of sensor device 500 to an exemplary anchoring means; in this example, sensor device 500 may be diffusion bonded, welded, brazed, soldered, or otherwise suitably attached to an inner side 505 of scaffold 504. Scaffold 504 may be a stent-like structure, which is a tubular device that is typically implanted in a damaged vessel or artery to maintain the opening of the vessel or artery, as described for example in U.S. Pat. No. 7,763,064 to Pinchasik. Scaffold 504 comprises inner side 505, an outer side 506, and a longitudinal axis 507. In some embodiments, scaffold 504 has a high degree of radial force in direction r, in order to hold a vessel or artery open. When a stent is used as scaffold 504 it is preferred that the stent provide sufficient radial resistance in direction r (see FIG. 5B) to hold the stent in a constant position in the vessel; i.e., to secure the sensor in the desired position. U.S. Pat. No. 7,763,064 to Pinchasik describes such scaffolds and is incorporated by reference in its entirety.

The scaffold 504 may be either self-expanding or expanded by an inflatable balloon. In one embodiment the scaffold is balloon expandable, and the delivery system includes an inflation lumen. An inflation balloon may be coaxially disposed on the outside of the cannula or catheter. Scaffold 504, including passive sensor 500, is crimped onto the inflation balloon for insertion and placement. After scaffold 504 is in place within the body, inflation balloon is inflated under the control of the operator. Scaffold 504 expands until it reaches a desired diameter within a vessel or area. The inflation balloon is then deflated and removed, leaving scaffold 504, including sensor device 500, within the vessel or area. Scaffold 504 comprises, for example, nitinol, stainless steel, cobalt chromium, or other biocompatible materials with sufficient elasticity and plasticity to expand under the force of inflation balloon and remain securely in place after expansion.

In another embodiment, scaffold 504 is made from Nitinol, or another self-expandable material that will expand, for example, under higher, in vivo, temperatures and pressures. For certain sensor devices, it may be desirable to deploy the sensor without the need for an inflation balloon to prevent damage to the attached sensor device. U.S. 2006/0122691 to Richter, for example, discusses such materials and their use in scaffolds and is incorporated by reference in its entirety.

Scaffold 504 comprises, for example, nitinol, stainless steel, cobalt chromium, or other biocompatible materials with sufficient elasticity and plasticity to expand under the force of inflation balloon inflating and remain securely in place after expansion. Typically, an animal body will respond to the presence of a foreign object, such as the scaffold 504, by forming neointima, which aids in securing the scaffold 504. U.S. patent publication no. 2006/0122691 to Richter, for example, discusses neointimal growth and securing scaffolds in place by burying the scaffold in neointima and is incorporated by reference in its entirety.

Figure 5B:
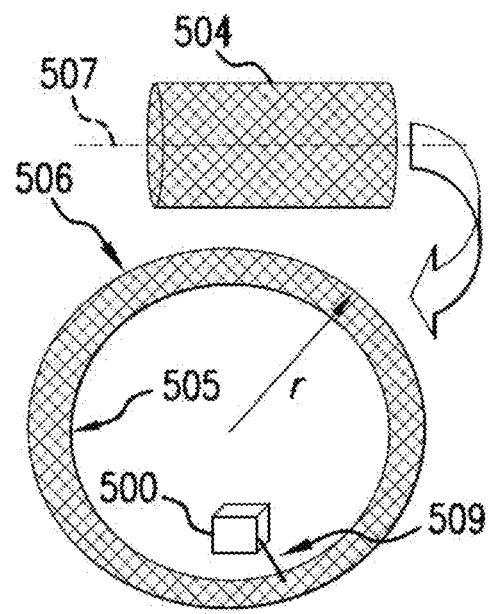
Figure 6A:
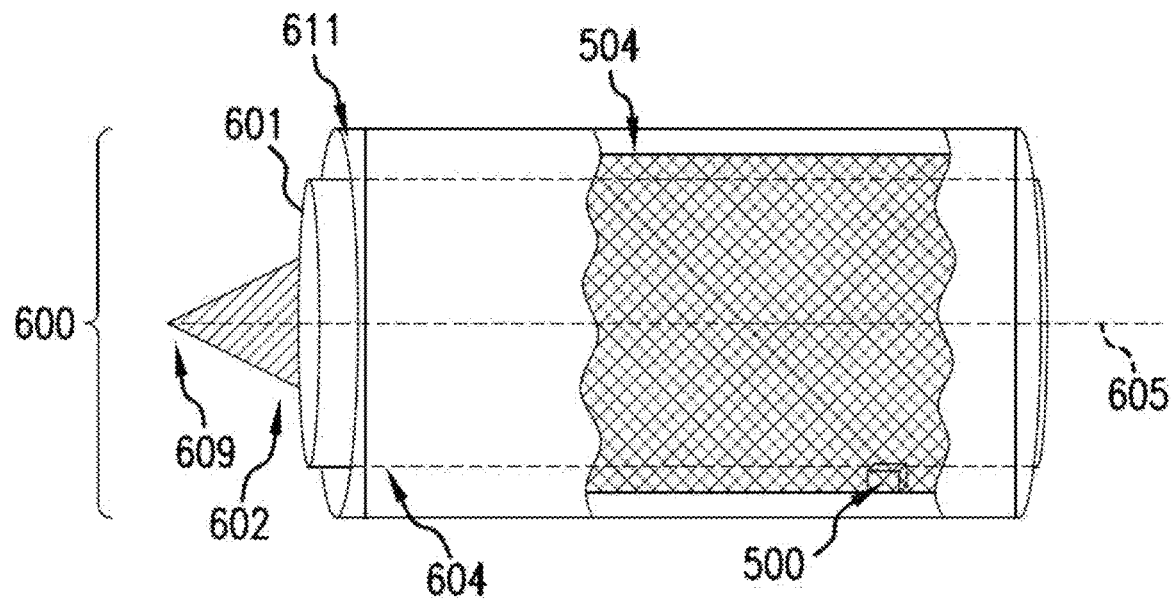
FIGS. 6A-6B show aspects of various embodiments of a passive sensor implantation device in accordance with the invention.
Figure 6B:
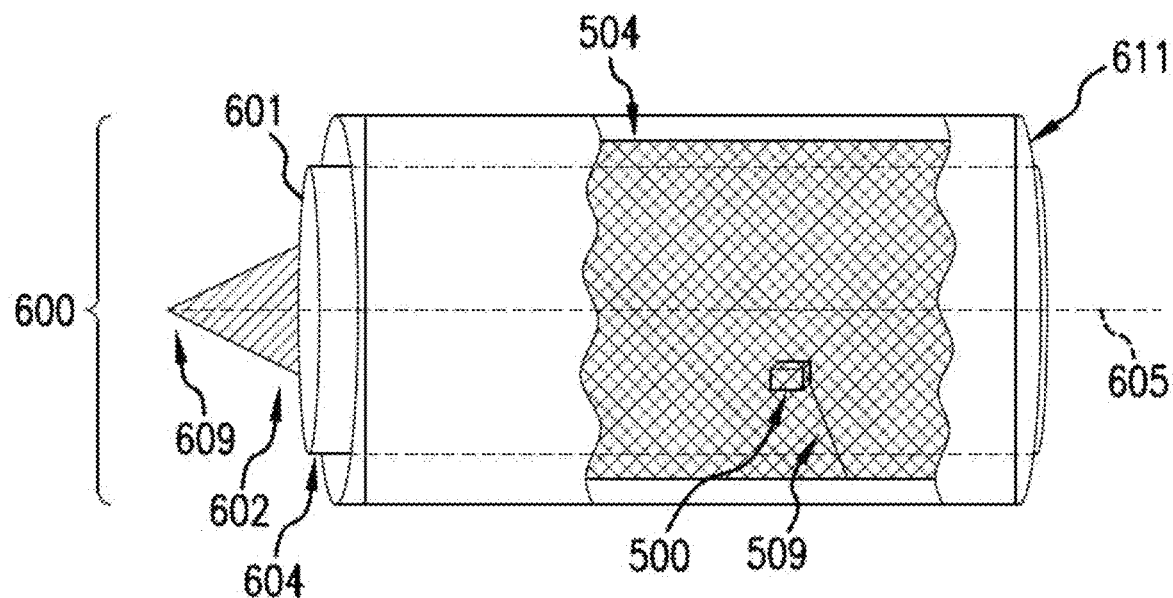

FIG. 5B shows an embodiment where sensor device 500 is tethered to scaffold 504 via a lead line 509, which is a stent strut, cable, wire, or other suitable material that is capable of resisting the force of blood-flow and potential influence on the position of the device, and is bioinert as herein discussed. A lead line is attached to sensor device 500 and scaffold 504 by welding, brazing, tying, adhesives, or the like, or may be an integral part of scaffold 504.

Figure 5C:
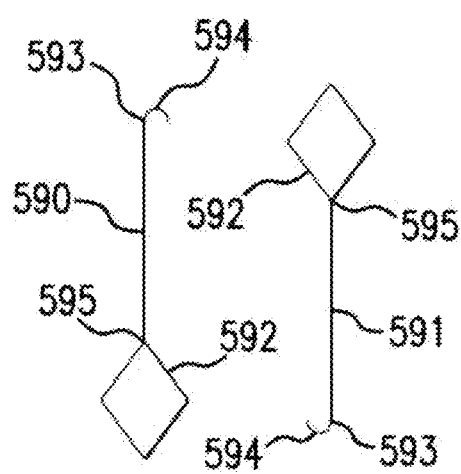

An alternative method of implanting a sensor device of the invention in a measurement environment involves the use of an anchoring mechanism other than a scaffold. FIG. 5C illustrates an embodiment for an anchoring mechanism from the prior art comprising a first support leg 590 and a second support leg 591 which are attached at a first end 595 to the sensor housing 592 of a sensor device of the invention. At a second end 593, each support leg 590, 591 has a protrusion 594 in the shape of a hook, or the like. The protrusions 594 of the anchoring mechanisms attach to the tissues or walls of vessels in which the sensor housing 592 is implanted, thereby securing the assembly.

The sensor of the invention may be delivered to the target site by various methods known in the art. Implantation into the portal vein may be done via a transhepatic puncture using either an intracostal or subxiphoid approach. Implantation may also be done using a transjugular approach that would necessitate an intrahepatic puncture from the hepatic to portal venous systems. FIGS. 6A and 6B show one embodiment of a delivery system 600 for use in delivering the sensor device 500 and attachment means to the sensing environment. As illustrated in FIGS. 6A and 6B the delivery system 600 comprises an intravenous cannula or catheter that includes an internal tube 604 having a lumen about a longitudinal axis 605 and an external or outer tube 611. A cut-away view of 611 in FIGS. 6A and 6B shows the scaffold 504 with the sensor 500 may be coaxially disposed about the internal tubular structure 604 of the delivery system, for example a cannula or catheter. In this embodiment, the scaffold 504 is self-expanding. As shown in FIGS. 6A and 6B, the scaffold 504 may be crimped around the internal tube 604 and held in the compressed delivery configuration by the outer tube 611. To deploy the scaffold 504, the outer tube 611 is removed to permit the scaffold 504 to expand and engage the vessel lumen. Once expanded the interior tube 604 may be withdrawn leaving the scaffold 504 in the vessel, with the sensor 500 exposed to the ambient fluid of the vessel. In the embodiment illustrated in FIGS. 6A-6B, the cannula 604 or catheter has at a distal end 601 a trocar 602 having a sharp tip 609 for puncturing the bodily tissues and organs is coaxially disposed inside the lumen of the cannula 601. Alternatively the cannula 604 or catheter on which the scaffold 504 is disposed may be threaded through a needle-based system, which is used to penetrate the tissue and into the appropriate vessel, and advanced to the location where the sensor device 500 is to be deployed. Preferably, the tip of the catheter has a soft, rounded tip.

FIG. 6A shows an embodiment, wherein the scaffold 504 and sensor device 500 depicted in FIG. 5A are mounted on the catheter delivery system 600 coaxially. FIG. 6B shows a similar delivery system for a sensor 500 attached to scaffold 504 by lead line 509. When the scaffold 504 is implanted and expanded, sensor 500 is engulfed by the bloodstream, for example.

Once in place, the sensor may be located by various methods known in the art. For example, the presence and the intensity of Doppler shifted sideband peaks in the frequency response of the sensor may be used to identify or locate the sensor in the body and to assist the centering of the interrogating ultrasound beam on the sensor(s). The sensor reflects the carrier frequency ultrasound signal (with Doppler shift) with much higher amplitude than any tissue in the human body, thus the identification and localization of the sensor and the centering of the interrogating beam may be performed by searching for a significant Doppler effect in the received signal. If the interrogating beam is scanned across the region in which the sensor is implanted or located, the beam is centered on the sensor when the sideband frequency's amplitude is maximal. When correlating a received signal to a pulse cycle measurement, the pulsatile pressure changes the signal amplitude of the Doppler sideband frequency (or frequencies) during the pulse cycle time. These pulsatile pressure induced sideband amplitude changes are present only in the signal reflected from the vibratable membranes of the sensor. Maximizing the amplitude of these pulsatile (periodic) amplitude changes may also be used by the system for sensor identification and for beam centering. Thus, the operator or user of the device may scan the interrogating beam in the region where the implanted sensor is assumed to be positioned and look for the presence of a sideband component (or components) at the expected frequency (or frequencies) having an amplitude which periodically varies in time at a rate similar to the blood pulse rate. In accordance with an embodiment of the invention, the pulsating sideband component may be visually detected on a display device coupled to the system. The interrogating beam may then be centered by carefully changing the beam direction and/or orientation in until the amplitude of the amplitude of the periodically varying sideband is maximal.

The system's operator may then carefully scan the interrogating beam position for fine-tuning the best beam position. The beam's position may be fine-tuned or optimized by slowly changing the beam direction and/or orientation until the amplitude of the sideband peak(s) is the maximized. By maximizing the sideband amplitude the operator may ensure a good signal to noise ratio by maximizing the received energy at the sideband frequency or frequencies. Maximizing the amplitude of sideband frequency (or frequencies) may also contribute to improving the signal-to-noise ratio and therefore the measurement accuracy and/or the inter-test and/or intra-test accuracy, repeatability and sensitivity. After beam centering, the operator may use the system for determining the blood pressure by determining the resonance frequency of the sensor(s) as disclosed in detail herein and computing the blood pressure from the determined resonance frequency (or frequencies).

It will be appreciated by persons having ordinary skill in the art that many variations, additions, modifications, and other applications may be made to what has been particularly shown and described herein by way of embodiments, without departing from the spirit or scope of the invention. Therefore, it is intended that the scope of the invention, as defined by the claims below, includes all foreseeable variations, additions, modifications, or applications.

What is claimed is:

1. A method for detecting fluid pressure from an implanted sensor device, the sensor device comprising:
    a vibratable sensor comprising a sensor membrane, wherein the sensor membrane has a thickness of at least one micron, and the vibratable sensor has a total volume of less than or equal to 0.3 cubic millimeters;
    a housing having a cavity into which the entire vibratable sensor is disposed, the housing having a foundation having a thickness and an orifice extending therethrough, the foundation holding the vibratable sensor inside the cavity;
    a bottom film disposed on the housing and enclosing the sensor membrane within the housing, wherein the bottom film is separated from the sensor membrane by the orifice, wherein the foundation is not in direct contact with the sensor membrane; the method comprising the steps of:
        subjecting the implanted device to ultrasonic vibrations;
        receiving vibrations generated by the device in response to the ultrasonic vibrations, the generated vibration including a vibration frequency;
        determining the resonance frequency of the device from the vibration frequency;
        determining the ambient pressure of fluid surrounding the device from the resonance frequency of the device.

2. The method of claim 1, wherein the resonance frequency is determined using a phase inversion algorithm.

3. The method according to claim 1, wherein the sensor membrane comprises titanium or silicon, and the bottom film comprises titanium.

4. A method for monitoring fluid pressure from a sensor device implanted in each of two separate fluid systems, wherein each sensor device comprises:
    a vibratable sensor comprising a sensor membrane, wherein the sensor membrane has a thickness of at least one micron, and the vibratable sensor has a total volume of less than or equal to 0.3 cubic millimeters;
    a housing having a cavity into which the entire vibratable sensor is disposed, the housing having a foundation having a thickness and an orifice extending therethrough, the foundation holding the vibratable sensor inside the cavity;
    a bottom film disposed on the housing and enclosing the sensor membrane within the housing, wherein the bottom film is separated from the sensor membrane by the orifice; wherein the foundation is not in direct contact with the sensor membrane, the method comprising:
        subjecting each device to ultrasonic vibrations;
        receiving vibrations generated by each device in response to the ultrasonic vibrations, each generated vibration including a vibration frequency;
        determining the resonance frequency of each device from the respective vibration frequency of each device;
        determining the ambient pressure of fluid surrounding each device from the resonance frequency of each device; and
        determining a pressure gradient between the devices.

5. The method of claim 4, wherein the resonance frequency is determined using a phase inversion algorithm.

6. The method of claim 4, further comprising displaying the pressure gradient.

7. The method of claim 4, wherein said method further includes monitoring the patency of a transjugular intrahepatic portosystemic shunt.

8. The method of claim 4, wherein determining the pressure gradient further comprises distinguishing each vibration frequency from noise.

9. The method of claim 8, wherein distinguishing each vibration frequency from noise comprises identifying an amplitude peak in each vibration frequency.

10. The method of claim 8, wherein distinguishing each vibration frequency from noise comprises:
    identifying a pulse cycle;
    receiving a plurality of vibration signals generated by each device during the pulse cycle;
    comparing the pulse cycle to the received signals; and,
    identifying a waveform that correlates to the pulse cycle.

11. A method for detecting ambient fluid pressure using a sensor device disposed in a fluid environment, wherein said device comprises:
    a vibratable sensor comprising a sensor membrane, wherein the sensor membrane has a thickness of at least one micron, and the vibratable sensor has a total volume of less than or equal to 0.3 cubic millimeters;
    a housing having a cavity into which the entire vibratable sensor is disposed, the housing having a foundation having a thickness and an orifice therethrough, the foundation holding the vibratable sensor inside the cavity;
    a bottom film disposed on the housing and enclosing the sensor membrane within the housing, wherein the bottom film is separated from the sensor membrane by the orifice;
    wherein the foundation is not in direct contact with the sensor membrane, the method comprising the steps of:

subjecting the device to ultrasonic vibrations;
receiving vibrations generated by the device in response to the ultrasonic vibrations, the generated vibration including a vibration frequency;
determining the resonance frequency of the device from the vibration frequency;
determining the ambient pressure of fluid surrounding the device from the resonance frequency of the device.

12. The method of claim 4, further comprising distinguishing each sensor by a unique frequency response for each sensor at a given pressure.

13. A method for detecting fluid pressure from a sensor device implanted in a fluid system, wherein the sensor device comprises:
a vibratable sensor comprising a sensor membrane, wherein the sensor membrane comprises silicon or titanium and has a thickness of at least one micron, and the vibratable sensor has a total volume of less than or equal to 0.3 cubic millimeters;
a housing having a cavity into which the entire vibratable sensor is disposed, the housing having a foundation which contains an orifice and holds the vibratable sensor inside the cavity;
a bottom film disposed on the housing and enclosing the sensor membrane within the housing, wherein the bottom film comprises titanium and is separated from the sensor membrane by the orifice; wherein the foundation is not in direct contact with the sensor membrane, the method comprising:
subjecting the device to ultrasonic vibrations;
receiving a vibration generated by the device, the generated vibration including a vibration frequency;
determining the resonance frequency of the device from the vibration frequency; and,
determining the ambient pressure of fluid surrounding the device from the resonance frequency of the device.

14. The method of claim 13, wherein the resonance frequency is determined using a phase inversion algorithm.

15. The method of claim 13, further comprising displaying the ambient pressure.

16. The method of claim 13, wherein determining the ambient pressure further comprises distinguishing the vibration frequency from noise.

17. The method of claim 16, wherein distinguishing the vibration frequency from noise comprises identifying an amplitude peak in the vibration frequency.

18. The method of claim 16, wherein distinguishing the vibration frequency from noise comprises:
identifying a pulse rate, and determining a pulse cycle which comprises at least one cycle of expansion and contraction of the heart;
receiving a plurality of vibration signals generated by the device during the pulse cycle;
comparing the pulse cycle to the received signals; and,
identifying a waveform that correlates to the pulse cycle.

19. The method of any one of claim 10 or 11, further comprising measuring the pulse cycle and waveform with an external device and correlating with an acquired pressure waveform from the sensor.

20. A method for detecting ambient fluid pressure from sensor devices disposed in each of two environments, wherein each device comprises:
a vibratable sensor comprising a sensor membrane, wherein the sensor membrane has a thickness of at least one micron, and the vibratable sensor has a total volume of less than or equal to 0.3 cubic millimeters;
a housing having a cavity into which the entire vibratable sensor is disposed, the housing having a foundation having a thickness and an orifice extending therethrough, the foundation holding the vibratable sensor inside the cavity;
a bottom film disposed on the housing and enclosing the sensor membrane within the housing, wherein the bottom film is separated from the sensor membrane by the orifice;
wherein the foundation is not in direct contact with the sensor membrane, the method comprising:
subjecting each device to ultrasonic vibrations;
receiving vibrations generated by each device in response to the ultrasonic vibrations, each generated vibration including a vibration frequency;
determining the resonance frequency of each device from the respective vibration frequency of each device;
determining the ambient pressure of fluid surrounding each device from the resonance frequency of each device; and
determining a pressure gradient between the devices.

* * * * *